United States Patent [19]

Belanger et al.

[11] 4,332,810
[45] Jun. 1, 1982

[54] N-(SUBSTITUTED)-2,5-ETHANO-8-HYDROXY (OR METHOXY)-1,2,3,4,5,6-HEXAHYDRO-3 (OR 4)-BENZAZOCINE CENTRALLY-ACTING ANALGESICS

[75] Inventors: Patrice C. Belanger, Dollard des Ormeaux; Robert N. Young, Senneville, both of Canada

[73] Assignee: Merck & Co., Inc., Rahway, N.J.

[21] Appl. No.: 228,483

[22] Filed: Jan. 26, 1981

[51] Int. Cl.³ .................. A61K 31/445; C07D 221/22
[52] U.S. Cl. ...................................... 424/267; 546/93; 564/265; 568/326
[58] Field of Search .......................... 546/93; 424/267

[56] References Cited

U.S. PATENT DOCUMENTS 3,513,169  5/1970  Robinson et al. ............... 546/97
3,514,463  5/1970  Robinson et al. ............... 546/97
3,700,734 10/1972  Robinson et al. ............... 546/97

OTHER PUBLICATIONS

Freed, M., et al., *J. Med. Chem.*, 16(6), 595–599, (1973).
*Chemical Abstracts*, 82:164804j (1975) [Walter, L., et al., *J. Med. Chem.* 1975, 18(2), 206–208].
Mitsuhashi, K., et al., *Chem. Pharm. Bull.* (Japan), 17, 434–453 (1969).

*Primary Examiner*—Richard A. Schwartz
*Attorney, Agent, or Firm*—Theresa Y. Cheng; Raymond M. Speer; Mario A. Monaco

[57] ABSTRACT

Novel N-(substituted) derivatives of 2,5-ethano-8-hydroxy (or methoxy)-1,2,3,4,5,6-hexahydro-3 (or 4)-benzazocine of the formula:

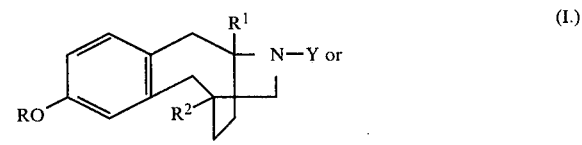

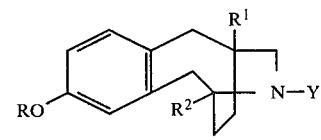

are centrally acting analgesics effective in the relief of pain.

14 Claims, No Drawings

N-(SUBSTITUTED)-2,5-ETHANO-8-HYDROXY (OR METHOXY)-1,2,3,4,5,6-HEXAHYDRO-3 (OR 4)-BENZAZOCINE CENTRALLY-ACTING ANALGESICS

BACKGROUND OF THE INVENTION

1. Field of the Invention

The present invention is concerned with novel centrally-acting analgesic agents, i.e., agents acting on opiate receptors within the central nervous system to produce potent and profound analgesia.

The most widely used centrally-acting analgesic continues to be morphine. This drug, however, has serious drawbacks as the result of certain pronounced side effects. Not only does use of morphine usually lead to physiological and psychological dependency, but morphine is a respiratory depressant as well.

Thus, there has been a continuous search for a centrally-acting analgesic with the potency of morphine, but without its dangerous side effects. For example, many analgesic agents based on the morphine model have been prepared. One of the best known of these is meperidine. While this drug was originally thought to be non-addicting, it was soon found to have dangerous addiction liability.

Other centrally-acting analgesics include the class of compounds known as the benzomorphans. Pentazocine, phenazocine, cyclazocine, ketocyclazocine, and ethylketocyclazocine are some of the better known members of this class of compounds. However, as with other centrally-acting analgesics developed heretofore, the benzomorphans also have undesirable addiction qualities.

2. Brief Description of the Prior Art

Robinson et. al., U.S. Pat. Nos. 3,700,734; 3,514,463; 3,513,169; and 3,499,906 describe benzomorphan derivatives having analgesic activity.

Freed et. al., U.S. Pat. Nos. 3,836,670; 4,001,331; and 4,076,953 describe benzobicycloalkane amines for inducing analgesia.

Co-pending U.S. Ser. No. 117,701, filed Feb. 19, 1980, describes derivatives of 2-hydroxy-6,9-methano-11-amino-5,6,7,8,9,10-hexahydrobenzocyclooctene.

However, none of the compounds disclosed in any of the above would suggest the novel compounds of the present invention to a person of ordinary skill in the art.

SUMMARY OF THE INVENTION

The present invention relates to novel N-(substituted) derivatives of 2,5-ethano-8-hydroxy (or methoxy)-1,2,3,4,5,6-hexahydro-3 (or 4)-benzazocine and pharmaceutically acceptable salts thereof.

The present invention also relates to a method of treating pain comprising administering to a patient (human or animal) in need of such treatment, a therapeutically effective amount of a novel compound of the present invention; as well as to a pharmaceutical composition for use in treating pain comprising a pharmaceutically acceptable carrier and a therapeutically effective amount of a novel compound of the present invention.

The present invention also relates to a method of preparing the novel compounds of the present invention, as well as to novel intermediates useful in said method.

The novel compounds of the present invention may be represented by the following formula:

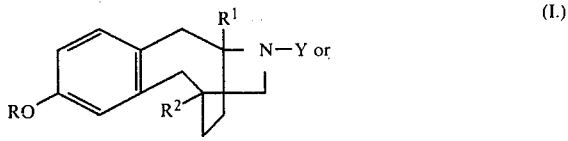

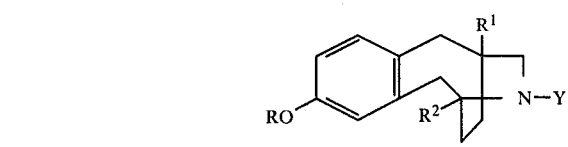

where
R is hydrogen or methyl;
$R^1$, and $R^2$, are each independently hydrogen or $C_{1-4}$alkyl; and
Y is (a) $C_{1-4}$alkyl; (b) $C_{1-4}$alkenyl; (c) $C_{3-4}$cycloalkylmethyl; (d) phenyl $C_{1-4}$alkyl; or (e)

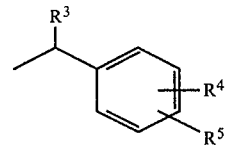

wherein:
$R^3$ is hydrogen or $C_{1-4}$alkyl; and
$R^4$ and $R^5$ are each independently selected from the group consisting of (1) hydrogen; (2) halo; (3) $C_{1-4}$alkyl; (4) $C_{1-4}$alkoxy; (5) amino, and mono- and di-$C_{1-4}$alkyl substituted amino; (6) cyano; (7) trifluoromethyl; (8) trifluoromethylthio; (9) $C_{1-4}$alkylthio; (10) $C_{1-4}$alkylsulfoxide; (11) $C_{1-4}$alkylsulfone; (12) hydroxy; and (13) phenyl;
and a pharmaceutically acceptable salt thereof.

The numbering of the N-(substituted)-2,5-ethano-8-hydroxy (or methoxy)-1,2,3,4,5,6-hexahydro-3 (or 4)-benzazocine compounds of the present invention is illustrated below:

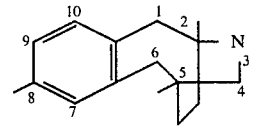

Included in this invention are the optical isomers of the compounds of Formula I, which may vary to some extent in their biological activity. Carbon atoms 2 and 5 are asymmetric.

These isomers can be separated into their optical isomers [dextro (+) and levo (−)] by preparing the diastereoisomeric salts with optically active acids, either D (+) or L (−), which salts can then be separated by conventional methods such as fractional crystallization. Thus, it is to be understood that included in this invention, in addition to racemic mixtures of the novel N-(substituted)-2,5-ethano-8-hydroxy (or methoxy)-1,2,3,4,5,6-hexahydro-3 (or 4)-benzazocine compounds, are the individual optical isomers, i.e., the dextrorotatory (+) and levorotatory (−) isomers of said novel compounds.

Among the novel compounds of the present invention, certain compounds are preferred. For example, the N-(substituted-benzyl) compounds are preferred, and the phenyl moiety substituents, $R^4$ and $R^5$, are preferred in the following order: para, meta, ortho, and it is preferred that there be only one such substituent. The most preferred substituents, in order of preference, are: methoxy, chloro, dimethylamine, hydrogen, and methyl.

It is preferred that the $R^1$, $R^2$, and $R^3$ substituents be hydrogen.

Representative compounds of the present invention are the following:

N-(4-chlorobenzyl)-2,5-ethano-8-hydroxy-1,2,3,4,5,6-hexahydro-3-benzazocine;
N-(4-methoxybenzyl)-2,5-ethano-8-hydroxy-1,2,3,4,5,6-hexahydro-3-benzazocine;
N-(4-dimethylaminobenzyl)-2,5-ethano-8-hydroxy-1,2,3,4,5,6-hexahydro-3-benzazocine;
N-benzyl-2,5-ethano-8-hydroxy-1,2,3,4,5,6-hexahydro-3-benzazocine;
N-(4-chlorobenzyl)-2,5-ethano-8-methoxy-1,2,3,4,5,6-hexahydro-3-benzazocine;
N-(4-methoxybenzyl)-2,5-ethano-8-methoxy-1,2,3,4,5,6-hexahydro-3-benzazocine;
N-(4-dimethylaminobenzyl-2,5-ethano-8-methoxy-1,2,3,4,5,6-hexahydro-3-benzazocine;
N-benzyl-2,5-ethano-8-methoxy-1,2,3,4,5,6-hexahydro-3-benzazocine;
N-(4-methoxybenzyl)-2,5-ethano-8-hydroxy-1,2,3,4,5,6-hexahydro-4-benzazocine;
N-(4-methoxybenzyl)-2,5-ethano-8-methoxy-1,2,3,4,5,6-hexahydro-4-benzazocine.

Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Water or oil-soluble or dispersible products are thereby obtained.

The novel compounds of the present invention are useful in alleviating pain in animal and human patients. For example, compounds of Formula I show good activity in a modified Randall Selitto test. Good activity in this test is accepted in the art as indicative of useful analgesic activity.

In addition, the compounds of the present invention show a reduction in the severity of the serious side effects associated with members of the morphine family of naturally occurring alkaloidal analgesics, such as addiction, tolerance, and respiratory depression. Moreover, unlike the morphine analgesics, the compounds of the present invention are orally active.

Various tests in animals have been carried out to show the ability of the compounds of this invention to exhibit reactions that can be correlated with activity in humans. One such test, outlined by Winter and Flataker in *J. Phar. Exp. Tera.*, 150, 1, pp. 165-171, shows the ability of the compounds of Formula I to exhibit analgesic effect. Measurements are made of the reaction threshold to pressure in the hind paws of rats injected with a phlogistic agent. These are compared with known analgesic drugs, and marked increased effects can be found. Drug dosages of up to 64 mg/kg are administered by the subcutaneous route. The experiments are carried out on Sprague-Dawley female rats weighing from 60 to 80 grams. The response threshold is determined by applying pressure to the foot and reading on a manometer the pressure at which an audible "squeak" is elicited. Groups of ten rats are used for each test and the average reading is recorded.

The N-(substituted)-2,5-ethano-8-hydroxy (or methoxy)-1,2,3,4,5,6-hexahydro-3 (or 4)-benzazocine compounds of the present invention generally have narcotic antagonist activity in varying degrees, as well as agonist activity. This mixture of agonist and antagonist activity can be advantageous since it is considered that this will result in reduced side effects.

Thus, the novel compounds of Formula I possess a high degree of analgesic activity, and are, accordingly, useful in treating animal and human patients experiencing moderate to severe pain originating from any one of a number of different sources.

The novel compounds of Formula I are also useful as anti-diarrheal and anti-tussive agents.

For these purposes the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcelluslose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the analgesic agents are employed.

Dosage levels of the order of 5 to 50 mg per day are useful in the treatment of the above indicated conditions. For example, analgesic activity is manifested by the administration of from about 0.1 to 1.0 milligrams of the compound per kilogram of body weight per day. Advantageously from about 0.05 mg to about 0.5 mg per kilogram of body weight per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 to 50 mg of active agent compounded with an appropriate and convenient amount of carrier material which may vary from about 5 to about 95 percent of the total composition. Dosage unit forms will generally contain between from about 2 mg to about 15 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The novel compounds of Formula I are conveniently prepared by the following methods from known starting materials.

The starting materials are 5,6,7,8,9,10-hexahydro-6,9-methanobenzocyclooctene-11-ones and are readily prepared by the reaction of $\alpha,\alpha'$-dihalo xylene or an appropriately substituted xylene and a cyclic ketone derivative. Thus, for example, reaction of $\alpha,\alpha'$-dibromo xylene and the pyrrolidine enamine of cyclopentanone or cyclohexanone in an aprotic solvent such as acetonitrile produces the desired 6,9-methanobenzocyclooctene-11-one or the corresponding benzocyclononen-11-one. In order to introduce the phenolic hydroxyl group into the cyclooctene-11-one compounds in a one-step reaction, the starting ketone is treated in strongly acid solution, preferably in trifluoroacetic acid, with thallium trifluoroacetate at a temperature of from 0°–50° C. and preferably between 10°–30° C. The reaction is allowed to proceed for a period of from 1–24 hours and is then treated with an oxidizing agent, as for example lead tetraacetate, and the resulting mixture is then stirred with heating, preferably at reflux temperature of the reaction mixture for a period of from 1–5 hours. The entire reaction mixture is then treated with triphenyl phosphine in order to free the hydroxy cyclooctene-11-one from its complex, and then the desired ketone purified by removal of the reaction solvent by evaporation under reduced pressure followed by extraction of the residual material with chloroform, and the chloroform extract washed with water and dried to yield the desired product, which is conveniently purified by crystallization from a solvent.

The phenolic hydroxyl compound prepared as just described can then be converted to the corresponding methoxy compound by reaction with a methylating agent such as dimethylsulfate or methyl iodide in the presence of a base such as potassium carbonate.

The hydroxy and methoxy 11-keto compounds prepared according to the previous procedure then become starting materials for a sequence of reactions which may be illustrated as follows:

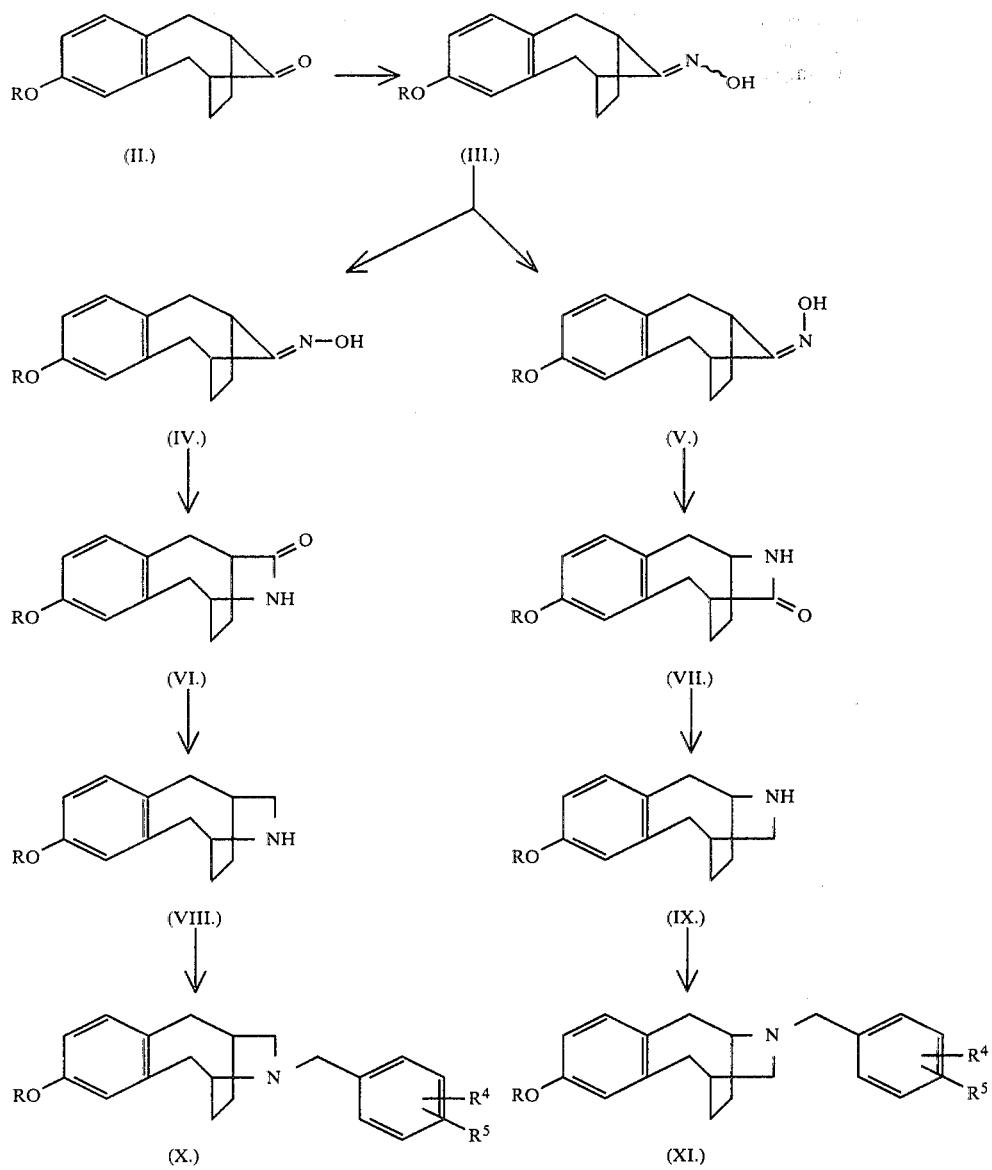

A. In the first reaction, the 11-keto compound (II) is refluxed with an approximately equimolar amount of hydroxylamine hydrochloride to form the corresponding 11-oximino compound (III). The reaction produces a mixture of syn- and anti-oximes.

B. The mixture of oxime geometrical isomers is separated by chromatography, for example on a Waters prep LC 500, eluting with hexane/acetate, 1:1 (v/v/, with two recycles. The anti-oxime (IV) and syn-oxime (V) are obtained.

C. The anti- and syn-oxime geometrical isomers are treated in a similar fashion with toluene-p-sulfonyl chloride in order to accomplish ring expansion by Beckmann rearrangement. The anti-oxime (IV) forms the 3-oxo-4-benzazocine (VI); and the syn-oxime (V) forms the 4-oxo-3-benzazocine, (VII). The incidental 8-tosyloxy group is then removed, for example, by treatment with sodium methoxide.

D. The 3-oxo-group is next removed by reducing with lithium aluminum hydride, and the 4-benzazocine (VIII) and 3-benzazocine (IX) compounds are produced.

E. In order to prepare the N-benzyl and N-(substituted-benzyl)compounds of the present invention, the 4-benzazocine (VIII) and 3-benzazocine (IX) may both be treated in one of the following ways:
- (a) the appropriately substituted benzaldehyde:
  - (1) with in the presence of sodium cyanoborohydride using methanol as solvent; or
  - (2) in the presence of platinum oxide under a hydrogen atmosphere using ethanol as solvent; or with:
- (b) the appropriately substituted benzyl halide in the presence of diisopropylamine using acetonitrile as solvent.

Compounds of the present invention (X) and (XI) are thereby produced, respectively.

In an alternative procedure, the chromatographic separation in B. above is eliminated while the other successive procedures are carried out on the mixture of geometrical isomers (IV) and (V). The methoxy group is maintained until the last step. This alternative procedure may be illustrated by the following reaction scheme:

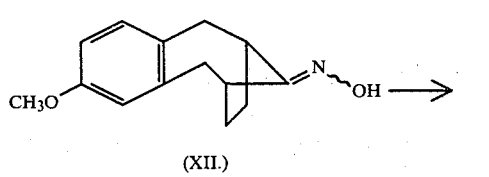

(XII.)

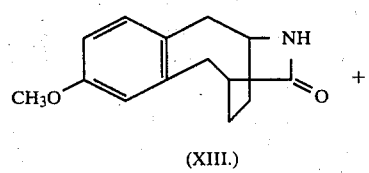

(XIII.)

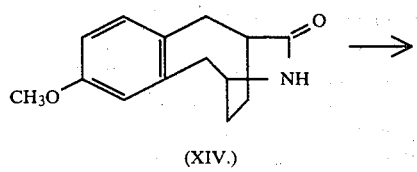

(XIV.)

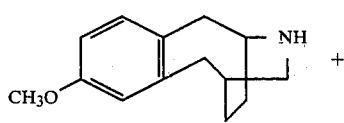

19
(XV.)

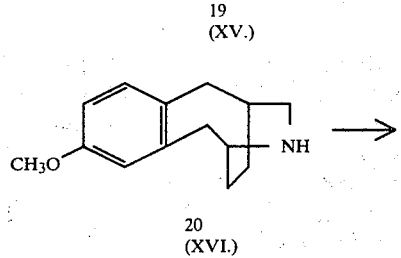

20
(XVI.)

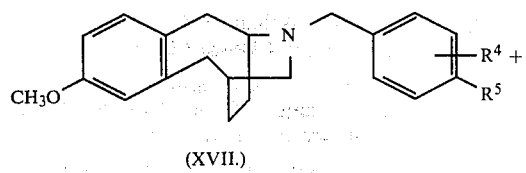

(XVII.)

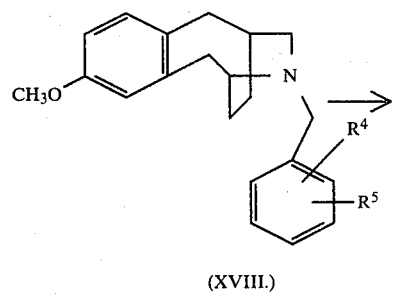

(XVIII.)

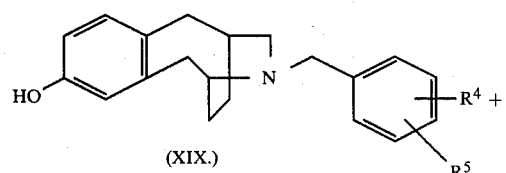

(XIX.)

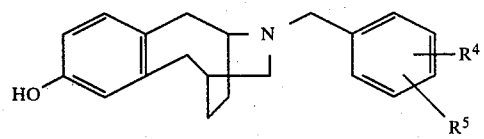

(XX.)

The compounds of the present invention wherein Y is $C_{1-4}$alkyl, $C_{1-4}$alkenyl, $C_{3-4}$cycloalkylmethyl, and phenyl $C_{1-4}$alkyl may be prepared by essentially the same process described above in E.(b), substituting for the benzyl halide an equivalent amount of the appropriate halide, for example, methyl iodide, allyl bromide, or phenethyl bromide.

A process for the preparation of the compounds of the present invention which are substituted by alkyl substituents, e.g., methyl substituents in the 2 and/or 5 positions, begins with the treatment of an α,α-dihaloxylene with an alkylated or dialkylated derivative of the appropriate cycloalkanone-enamine. Thus, for example, α,α-dibromoxylene is treated with the pyrrolidine enamine of 2,5-dimethylcyclopentanone to produce the corresponding 6,9-dimethyl-5,6,7,8,9,10-hexahydro-6,9-methanobenzocyclooctene-11-one, followed by thallation as described hereinabove, to introduce the corresponding 2'-hydroxy compound and subsequent conversion to the oxime.

The novel intermediates of the present invention are the compounds produced by ring expansion, and subsequent reduction (VIII and IX): 2,5-ethano-8-methoxy-1,2,3,4,5,6-hexahydro-3-benzazocine; 2,5-ethano-8-hydroxy-1,2,3,4,5,6-hexahydro-3-benzazocine; 2,5-ethano-8-methoxy-1,2,3,4,5,6-hexahydro-4-benzazocine; and 2,5-ethano-8-hydroxy-1,2,3,4,5,6-hexahydro-4-benzazocine.

The following examples illustrate preparation of various of the novel compounds of the present invention, but are not intended to in any way be a limitation thereof.

EXAMPLE 1

N-(4-Chlorobenzyl)-2,5-ethano-8-hydroxy-1,2,3,4,5,6-hexahydro-4-benzazocine

Step A. Syn- and Anti-2-hydroxy-11-oximino-6,9-methano-5,6,7,8,9,10-hexahydro benzocyclooctene 2-Hydroxy-11-oxo-6,9-methano-5,6,7,8,9,10-hexahydrobenzocyclooctene (20.2 g; 0.1 mole), hydroxylamine hydrochloride (20.2 g; 0.29 mole) are refluxed in a mixture of ethanol (200 ml) and pyridine (50 ml) for a period of 3 hours. The volatiles are evaporated in vacuo. The residue is taken up in ether, washed with water, dried ($Na_2SO_4$) and concentrated in vacuo.

The residue (24 g) is purified by chromatography on silica gel using 5% methanol in chloroform to yield 13 g (60%) of the mixture of syn and anti oximes.

The mixture is chromatographed on a Waters prep LC 500, eluting with hexane/ethyl acetate 1/1 v/v, with two recycles.

7.3 g of the top isomer (anti) is obtained.
IR: 3300 $cm^{-1}$ [OH−]; 1680 $cm^{-1}$ [C═N]
7.6 g of the lower isomer (syn) is also obtained.
IR: 3320 $cm^{-1}$ [OH−1]; 1690 $cm^{-1}$ [C═N]

Step B-1
2,5-Ethano-8-hydroxy-3-oxo-1,2,3,4,5,6-hexahydro-4-benzazocine

Anti 2-hydroxy-11-oximino-6,9-methano-5,6,7,8,9,10-hexahydro benzocyclooctene prepared in Step A above (3 g; 13.8 mmoles) and tosyl chloride (5.8 g; 30.4 mmoles) in pyridine (50 ml) are stirred at room temperature overnight. The reaction mixture is concentrated in vacuo to a residue that is purified by chromatography to yield 3.58 g (70%) of 2,5-ethano-3-oxo-1,2,3,4,5,6-hexahydro-8-tosyloxy-4-benzazocine as an oil.

IR: 3400 $cm^{-1}$ [OH−]; 1670 $cm^{-1}$ [C═O]

The tosyl derivative is dissolved in methanol (50 ml) and sodium methoxide (4.5 g; 78.9 mmoles) is added. The reaction mixture is then stirred overnight. 3 N hydrochloric acid (35 ml) is added and the reaction mixture is extracted twice with chloroform. The combined organic layers are washed with water, dried ($Na_2SO_4$) and concentrated in vacuo to yield an oil that is triturated in water. The crystals are filtered and pumped in vacuo for several hours to yield the title compound, m.p. 241°–245° C.

IR: 3400 $cm^{-1}$ [OH−1]; 3300 $cm^{-1}$ [NH]; 1650 $cm^{-1}$ [C═O]

Step B-2
2,5-Ethanol-8-hydroxy-4-oxo-1,2,3,4,5,6-hexahydro-3-benzozocine

Similarly, syn-2-hydroxy-11-oximino-6,9-methano-5,6,7,8,9,10-hexahydrobenzocyclooctene prepared in Step A above (3.0 g; 13.8 mmoles) is treated with tosyl chloride (5.8 g; 30.4 mmoles) followed by sodium methoxide to yield 1.66 g of the title compound, m.p. 305°–309° C.

IR: 3400 $cm^{-1}$ [OH−]; 3320 $cm^{-1}$ [NH]; 1650 $cm^{-1}$ [C═O]

Step C-1
2,5-Ethano-8-hydroxy-1,2,3,4,5,6-hexahydro-4-benzazocine

To a solution of 2,5-ethano-3-oxo-1,2,3,4,5,6-hexahydro-8-hydroxy-4-benzazocine (1.4 g; 6.45 mmoles) prepared in Step B-1 above, in tetrahydrofuran (65 ml) is added in small portions lithium aluminium hydride (1.2 g; 32 mmoles). The mixture is refluxed overnight. The reaction mixture is then treated with a saturated ammonium chloride solution (3 ml) and then with 1 N sodium bicarbonate (8 ml). The mixture is stirred for 15 minutes and then filtered. The filtrate is concentrated in vacuo. The oil is taken up in methanol, treated with hydrogen chloride and evaporated to dryness. The residue is triturated in ether to yield 1.33 g of a solid which, after recrystallization from methanol/chloroform, melts at 275° C.

Anal. Calc. for $C_{13}H_{17}NO \cdot HCl$: C: 65.12; H: 7.56; N: 5.84; Cl: 14.78. Found: C: 65.09; H: 7.60; N: 5.77; Cl: 15.37.

Step C-2
2,5-Ethano-8-hydroxy-1,2,3,4,5,6-hexahydro-3-benzazocine

Similarly, 2,5-ethano-8-hydroxy-4-oxo-1,2,3,4,5,6-hexahydro-3-benzazocine (1.54 g; 7.07 mmoles) prepared in Step B-2 above, in tetrahydrofuran (70 ml) is reduced by lithium aluminium hydride (1.34 g; 35 mmoles) to yield 1.04 g (62%) of the title compound, m.p. 234°–240° C.

Anal. Calcd for $C_{13}H_{17}NO \cdot HCl$: C: 65.12; H: 7.56; N: 5.84; Cl: 14.78. Found: C: 64.56; H: 7.65; N: 5.65; Cl: 14.69.

Step D
N-(4-chlorobenzyl)-2,5-ethano-8-hydroxy-1,2,3,4,5,6-hexahydro-4-benzazocine To 2,5-ethanol-8-hydroxy-1,2,3,4,5,6-hexahydro-4-benzazocine (1.4 g; 5.8 mmoles) prepared in Step C-1 above in methanol (56 ml) is added p-chlorobenzaldehyde (8 g; 57 mmoles) and sodium cyanoborohydride (2.9 g; 46 mmoles). The mixture is stirred at room temperature overnight. 1 N sodium bicarbonate (55 ml) and water (30 ml) is then added and the mixture is extracted several times with chloroform. The organic layer is dried ($Na_2SO_4$) and concentrated in vacuo to yield a residue that is purified by chromatography on silica gel. Elution with chloroform yields 1.3 g of an oil that crystallizes slowly. It is taken up in methanol, treated with hydrogen chloride to yield 812 mg of the title compound, m.p. 282°–290° C.

Anal. Calcd for $C_{20}H_{22}NOCl \cdot HCl$: C: 65.93; H: 6.36; N: 3.84; Cl: 19.46. Found: C: 66.03; H: 6.20; N: 3.79; Cl: 19.49.

EXAMPLE 2

N-(4-Methoxybenzyl)-2,5-ethano-8-hydroxy-1,2,3,4,5,6-hexahydro-4-benzazocine

Following the procedures of Example 1, Step D, 2,5-ethanol-8-hydroxy-1,2,3,4,5,6-hexahydro-4-benzazocine (1.2 g; 5.9 mmoles) is reacted with p-anisaldehyde (7.2 g; 53 mmoles) and sodium cyanoborohydride (1.48 g; 23.6 mmoles) in methanol (50 ml) to yield 1.0 g of the title compound, m.p. 250° C.

Anal. Calcd for $C_{21}H_{25}NO_2 \cdot HCl$: C: 70.08; H: 7.28; N: 3.89; Cl: 9.85. Found: C: 69.84; H: 7.53; N: 3.68; Cl: 9.63.

EXAMPLE 3

N-(4-chlorobenzyl)-2,5-ethano-8-hydroxy-1,2,3,4,5,6-hexahydro-3-benzazocine

Following the procedures of Example 1, Step D, 2,5-ethano-8-hydroxy-1,2,3,4,5,6-hexahydro-3-benzazocine (1.17 g; 4.89 mmoles) prepared in Example 1, Step C-2 above, is treated with p-chlorobenzaldehyde (6.9 g; 49 mmoles) and sodium cyanoborohydride (2.46 g; 39 mmoles) in methanol (50 ml) to yield 644 mg of the title compound, m.p. 175° C. (dec.).

Anal. Calcd for $C_{20}H_{22}NOCl.HCl.\frac{1}{4}H_2O$: C: 64.35; H: 6.48; N: 3.75; Cl: 19.00. Found: C: 64.22; H: 6.36; N: 3.75; Cl: 19.01.

EXAMPLE 4

N-(4-Methoxybenzyl)-2,5-ethano-8-hydroxy-1,2,3,4,5,6-hexahydro-3-benzazocine

Following the procedures of Example 1, Step D, 2,5-ethano-8-hydroxy-1,2,3,4,5,6-hexahydro-3-benzazoxine (1.3 g; 6.4 mmoles) prepared in Example 1, Step C-2 above, is reacted with p-anisaldehyde (7.8 g; 57.6 mmoles) and sodium cyanoborohydride (1.6 g; 25.6 mmoles) in methanol (50 ml) to yield 1.5 g (66%) of the title compound, m.p. 237° C. (dec.).

Anal. Calcd for $C_{21}H_{25}NO_2.HCl$: C: 70.08; H: 7.28; N: 3.89; Cl: 9.85. Found: C: 70.24; H: 7.44; N: 3.75; Cl: 9.75.

EXAMPLE 5

N-(4-Chlorobenzyl)-2,5-ethano-8-hydroxy-1,2,3,4,5,6-hexahydro-3-benzazocine and
N-(4-Chlorobenzyl)-2,5-ethano-8-hydroxy-1,2,3,4,5,6-hexahydro-4-benzazocine

Step A.

2-Methoxy-11-oximino-5,6,7,8,9,10-hexahydro-6,9-methanobenzocyclooctene

2-Methoxy-11-oxo-5,6,7,8,9,10-hexahydro-6,9-methanobenzocyclooctene (20.0 g; 0.1 mole) is reacted with hydroxylamine hydrochloride (20.0 g; 0.29 mole) in ethanol (100 ml) and pyridine (100 ml) to yield 20.1 g of the title compound.

IR: 3300 cm$^{-1}$ [OH$^-$]; 1635 cm$^{-1}$ [C≡N]

Step B.

2,5-Ethano-8-methoxy-3-oxo-1,2,3,4,5,6-hexahydro-4-benzazocine and
2,5-Ethano-8-methoxy-4-oxo-1,2,3,4,5,6-hexahydro-3-benzazocine Following the procedures in Example 1, Step B-1, 2-methoxy-11-oximino-5,6,7,8,9,10-hexahydro-6,9-methanobenzocyclooctene (21 g; 0.09 mole) prepared in Step A above is reacted with tosyl chloride (20 g; 0.105 mole) in pyridine (400 ml) to yield 16 g (77%) of the mixture of title compounds.

IR: 3180 cm$^{-1}$ [NH]; 1665 cm$^{-1}$ [C=O]

Step C.

2,5-Ethano-8-methoxy-1,2,3,4,5,6-hexahydro-3-benzazocine and
2,5-Ethano-8-methoxy-1,2,3,4,5,6-hexahydro-4-benzazocine Following the procedures of Example 1, Step C-1, the mixture of 2,5-ethano-8-methoxy-3-oxo-1,2,3,4,5,6-hexahydro-4-benzazocine and 2,5-ethano-8-methoxy-4-oxo-1,2,3,4,5,6-hexahydro-3-benzazocine (10.5 g; 0.045 mole) prepared in Step B above is reduced by lithium aluminium hydride (3.0 g; 0.079 mole) in tetrahydrofuran (200 ml) to yield 9.7 g (99%) of the mixture of the title compounds as an oil. IR: complete disappearance of [C=O] at 1665 cm$^{-1}$.

Step D.

N-(4-Chlorobenzyl)-2,5-ethano-8-methoxy-1,2,3,4,5,6-hexahydro-3-benzazocine and
N-(4-Chlorobenzyl)-2,5-ethano-8-methoxy-1,2,3,4,5,6-hexahydro-3-benzazocine (a) Alkylation with p-chlorobenzyl chloride To a mixture of 2,5-ethano-8-methoxy-1,2,3,4,5,6-hexahydro-3-benzazocine and 2,5-ethano-8-methoxy-1,2,3,4,5,6-hexahydro-4-benzazocine (9.0 g; 41.7 mmoles) prepared in Step C above, dissolved in acetonitrile (200 ml) is added diisopropylethylamine (10 ml) and p-chlorobenzylchloride (6.4 g; 39.3 mmoles). The reaction mixture is refluxed overnight. The volatiles are removed in vacuo and the residue is chromatographed on silica gel. Elution with 5% methanol in chloroform yields 10 g (71%) of the title compounds as an oil.

(b) Reductive alkylation with p-chlorobenzaldehyde

A mixture of 2,5-ethano-8-methoxy-1,2,3,4,5,6-hexahydro-3-benzazocine and 2,5-ethano-8-methoxy-1,2,3,4,5,6-hexahydro-4-benzazocine (10 g; 46.1 mmoles) is treated with p-chlorobenzaldehyde (5.6 g; 46.7 mmoles) and with sodium cyanoborohydride (3.0 g; mmoles) in methanol (150 ml) to yield 9.0 g (65%) of the title compounds as an oil.

(c) Reductive alkylation using hydrogen/platinum oxide

A mixture of 2,5-ethano-8-methoxy-1,2,3,4,5,6-hexahydro-3-benzazocine and 2,5-ethano-8-methoxy-1,2,3,4,5,6-hexahydro-4-benzazocine (0.65 g; 3 mmoles) and p-chlorobenzaldehyde (0.5 g; 41.7 mmoles) in methanol (30 ml) is hydrogenated in the presence of Adam's catalyst (30 mg) at room temperature for 24 hours. The catalyst is then removed, and the filtrate is evaporated to dryness to yield a residue which is purified by preparative thin layer chromatography. Development with 5% methanol in chloroform yields 0.5 g (50%) of a mixture of the title compounds.

Step E.

N-(4-Chlorobenzyl)-2,5-ethano-8-hydroxy-1,2,3,4,5,6-hexahydro-3-benzazocine and
N-(4-Chlorobenzyl)-2,5-ethano-8-hydroxy-1,2,3,4,5,6-hexahydro-4-benzazocine The mixture of N-(4-chlorobenzyl)-2,5-ethano-8-methoxy-1,2,3,4,5,6-hexahydro-3-benzazocine and N-(4-chlorobenzyl)-2,5-ethano-8-methoxy-1,2,3,4,5,6-hexahydro-4-benzazocine (10 g; 29.2 mmoles) prepared in Step D above, in 48% hydrobromic acid (200 ml) and in acetic acid (100 ml) is refluxed overnight. The mixture is poured into water, neutralized with 10 N sodium hydroxide and extracted several times with methylene chloride. The combined organic fractions are washed with water, dried (Na$_2$SO$_4$) and concentrated to dryness. The residue is chromatographed on silica gel. Elution with 2% methanol in chloroform containing 0.5% concentrated ammonia yields 2.0 g of the 3-benzazocine and 1.4 g of the 4-benzazocine as well as 3.8 g of a mixture of the title compounds, identical to the material prepared in Example 1, Step D, and Example 3.

IR: 3300 cm$^{-1}$ [OH$^-$]

What is claimed is:

1. A compound of the formula:

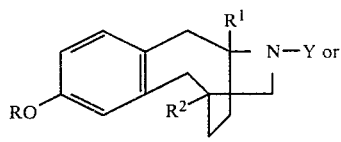

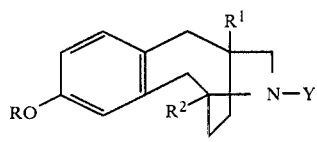

where
R is hydrogen or methyl;
$R^1$, and $R^2$, are each independently hydrogen or $C_{1-4}$ alkyl; and
Y is (a) $C_{1-4}$alkyl; (b) $C_{1-4}$alkenyl; (c) $C_{3-4}$cycloalkylmethyl; (d) phenyl $C_{1-4}$alkyl; or (e)

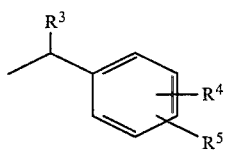

wherein:
$R^3$ is hydrogen or $C_{1-4}$alkyl; and
$R^4$ and $R^5$ are each independently selected from the group consisting of (1) hydrogen; (2) halo; (3) $C_{1-4}$ alkyl; (4) $C_{1-4}$ alkoxy; (5) amino, and mono- and di-$C_{1-4}$ alkyl substituted amino; (6) cyano; (7) trifluoromethyl; (8) trifluoromethylthio; (9) $C_{1-4}$ alkylthio; (10) $C_{1-4}$ alkylsulfoxide; (11) $C_{1-4}$ alkylsulfone; (12) hydroxy; and (13) phenyl;
or a pharmaceutically acceptable salt thereof.

2. A compound according to claim 1 wherein the compound is N-(4-chlorobenzyl)-2,5-ethano-8-hydroxy-1,2,3,4,5,6-hexahydro-3-benzazocine.

3. A compound according to claim 1 wherein the compound is N-(4-methoxybenzyl)-2,5-ethano-8-hydroxy-1,2,3,4,5,6-hexahydro-3-benzazocine.

4. A compound according to claim 1 wherein the compound is N-(4-dimethylaminobenzyl)-2,5-ethano-8-hydroxy-1,2,3,4,5,6-hexahydro-3-benzazocine.

5. A compound according to claim 1 wherein the compound is N-benzyl-2,5-ethano-8-hydroxy-1,2,3,4,5,6-hexahydro-3-benzazocine.

6. A compound according to claim 1 wherein the compound is N-(4-chlorobenzyl)-2,5-ethano-8-methoxy-1,2,3,4,5,6-hexahydro-3-benzazocine.

7. A compound according to claim 1 wherein the compound is N-(4-methoxybenzyl)-2,5-ethano-8-methoxy-1,2,3,4,5,6-hexahydro-3-benzazocine.

8. A compound according to claim 1 wherein the compound is N-(4-dimethylaminobenzyl-2,5-ethano-8-methoxy-1,2,3,4,5,6-hexahydro-3-benzazocine.

9. A compound according to claim 1 wherein the compound is N-benzyl-2,5-ethano-8-methoxy-1,2,3,4,5,6-hexahydro-3-benzazocine.

10. A compound according to claim 1 wherein the compound is N-(4-methoxybenzyl)-2,5-ethano-8-hydroxy-1,2,3,4,5,6-hexahydro-4-benzazocine.

11. A compound according to claim 1 wherein the compound is N-(4-methoxybenzyl)-2,5-ethano-8-methoxy-1,2,3,4,5,6-hexahydro-4-benzazocine.

12. A method of treating pain comprising administering to a patient in need of such treatment of therapeutically effective amount of a compound of the formula:

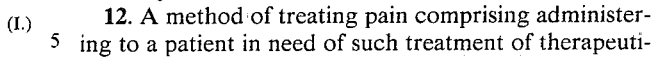

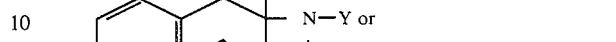

where
R is hydrogen or methyl;
$R^1$, and $R^2$, are each independently hydrogen or $C_{1-4}$ alkyl; and
Y is (a) $C_{1-4}$alkyl; (b) $C_{1-4}$alkenyl; (c) $C_{3-4}$cycloalkylmethyl; (d) phenyl $C_{1-4}$alkyl; or (e)

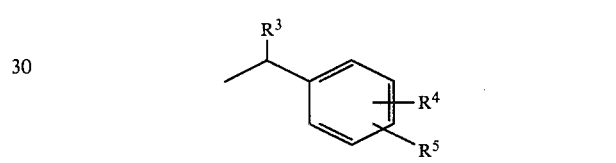

wherein:
$R^3$ is hydrogen or $C_{1-4}$alkyl; and
$R^4$ and $R^5$ are each independently selected from the group consisting of (1) hydrogen; (2) halo; (3) $C_{1-4}$ alkyl; (4) $C_{1-4}$ alkoxy; (5) amino, and mono- and di-$C_{1-4}$ alkyl substituted amino; (6) cyano; (7) trifluoromethyl; (8) trifluoromethylthio; (9) $C_{1-4}$ alkylthio; (10) $C_{1-4}$ alkylsulfoxide; (11) $C_{1-4}$ alkylsulfone; (12) hydroxy; and (13) phenyl;
or a pharmaceutically acceptable salt thereof.

13. A method according to claim 12 wherein the amount administered is from 5 to 50 mg per day.

14. A pharmaceutical composition for use in treating pain comprising a pharmaceutically acceptable carrier and a therapeutically effective amount of compound of the formula:

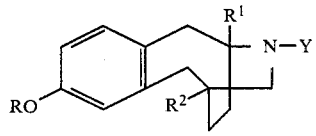

or

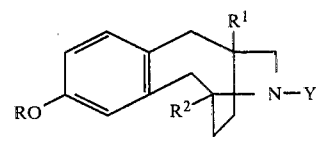

where
R is hydrogen or methyl;

$R^1$ and $R^2$ are each independently hydrogen or $C_{1-4}$alkyl; and

Y is (a) $C_{1-4}$alkyl; (b) $C_{1-4}$alkenyl; (c) $C_{3-4}$cycloalkylmethyl; (d) phenyl $C_{1-4}$alkyl; or (e)

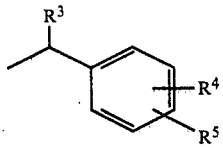

wherein:

$R^3$ is hydrogen or $C_{1-4}$alkyl; and $R^4$ and $R^5$ are each independently selected from the group consisting of
(1) hydrogen;
(2) halo;
(3) $C_{1-4}$ alkyl;
(4) $C_{1-4}$alkoxy;
(5) amino, and mono- and di-$C_{1-4}$alkyl substituted amino;
(6) cyano;
(7) trifluoromethyl;
(8) trifluoromethylthio;
(9) $C_{1-4}$alkylthio;
(10) $C_{1-4}$alkylsulfoxide;
(11) $C_{1-4}$alkylsulfone;
(12) hydroxy; and
(13) phenyl;

or a pharmaceutically acceptable salt thereof.

* * * * *